United States Patent
Leipold et al.

(10) Patent No.: US 8,444,771 B2
(45) Date of Patent: May 21, 2013

(54) METHOD FOR CLEANING AND/OR DEODORIZING TOILET BOWL OR URINAL USING AN ADHESIVE AGENT

(75) Inventors: Joachim Leipold, Reutlingen (DE); Edgar Jaeschke, Filderstadt (DE); Matthias Fritz, Gomaringen (DE)

(73) Assignee: Buck-Chemie GmbH, Herrenberg (DE)

(*) Notice: Subject to any disclaimer, the term of this patent is extended or adjusted under 35 U.S.C. 154(b) by 116 days.

(21) Appl. No.: 12/925,887

(22) Filed: Nov. 2, 2010

(65) Prior Publication Data

US 2011/0142784 A1    Jun. 16, 2011

Related U.S. Application Data

(63) Continuation-in-part of application No. 12/735,987, filed as application No. PCT/EP2009/000873 on Feb. 9, 2009.

(30) Foreign Application Priority Data

Feb. 29, 2008  (DE) .......................... 10 2008 012 092
Oct. 14, 2008  (DE) .......................... 10 2008 051 173

(51) Int. Cl.
- *B08B 9/093* (2006.01)
- *B08B 7/00* (2006.01)
- *A61L 9/05* (2006.01)
- *C11D 17/00* (2006.01)
- *C11D 3/37* (2006.01)

(52) U.S. Cl.
USPC ............. 134/22.18; 134/22.19; 134/2; 134/6; 134/42; 422/5; 510/191; 510/192; 510/193; 424/76.7

(58) Field of Classification Search
USPC ... 134/2, 6, 42, 22.18, 22.19; 422/5; 510/191, 510/192, 193; 424/76.7
See application file for complete search history.

(56) References Cited

U.S. PATENT DOCUMENTS

| | | | |
|---|---|---|---|
| 3,297,476 A * | 1/1967 | Kane ............................ | 428/457 |
| 5,783,541 A * | 7/1998 | Tack et al. ..................... | 510/224 |
| 6,667,286 B1 * | 12/2003 | Dettinger et al. ............. | 510/191 |
| 7,288,507 B2 | 10/2007 | McGee et al. | |
| 2005/0202988 A1 * | 9/2005 | De Belder et al. ............ | 510/191 |
| 2006/0024372 A1 | 2/2006 | Utterberg et al. | |
| 2007/0021566 A1 * | 1/2007 | Tse et al. ...................... | 525/240 |
| 2011/0002871 A1 | 1/2011 | Leipold | |

FOREIGN PATENT DOCUMENTS

| | | | |
|---|---|---|---|
| DE | 17 94 123 | A1 | 4/1972 |
| DE | 100 48 887 | A1 | 4/2002 |
| DE | 103 27 138 | A1 | 1/2005 |
| DE | 103 33 905 | A1 | 2/2005 |
| DE | 10 2004 056 554 | A1 | 5/2006 |
| DE | 10 2007 005 617 | A1 | 8/2008 |
| EP | 0 850 649 | A1 | 7/1998 |
| EP | 1 318 191 | B1 | 6/2003 |
| EP | 1 418 225 | A1 | 5/2004 |
| EP | 0 844 303 | B1 | 5/2005 |
| EP | 1 325 103 | B1 | 3/2006 |
| JP | 2001 270996 | A | 10/2001 |
| JP | 2004 067720 | A | 3/2004 |
| WO | WO 99/66017 | A1 | 12/1999 |
| WO | WO 99/66021 | A1 | 12/1999 |
| WO | WO 00/23558 | A1 | 4/2000 |
| WO | WO 00/58434 | A1 | 10/2000 |
| WO | WO 03/035511 | A1 | 5/2003 |
| WO | WO 2008/058853 | A1 | 5/2008 |

OTHER PUBLICATIONS

Unpublished U.S. Appl. No. 12/925,943, inventors Joachim Leipold, Edgar Jaeschke and Matthias Fritz, filed Nov. 2, 2010.
Mazol PGO 31K triglycerol monooleate, BASF Corporation, Florham Park, New Jersey (2009).
"Handbuch," p. 29, Pall Corporation, Port Washington, NY.
Kraton Sicherheitsdatenblatt, Kraton Polymers LLC, Houston, TX (2009).
Escorez 5000 Series petroleum hydrocarbon resin, Exxon Mobile, Breda, Netherlands (2008).
Irganox 1010 phenolic primary antioxidant data sheet, Ciba Specialty Chemicals (1998).
http://de.wikipedia.org/wiki/Seife.
http://de.wikipedia.org/wiki/Magnesiumstearat.
http://de.wikipedia.org/wiki/Kalkseife.

* cited by examiner

*Primary Examiner* — Lorna M Douyon
(74) *Attorney, Agent, or Firm* — Kriegsman & Kriegsman

(57) ABSTRACT

Method for cleaning and/or deodorizing a toilet bowl or urinal. In one embodiment, the method involves directly applying an agent to the toilet bowl or urinal. The agent adheres to the toilet bowl or urinal and can be flushed away only after a relatively large number of flushing operations. The agent includes fillers from the group of surfactants and also an adhesion promoter. The viscosity of the agent is at least 30 Pas, measured using a Haake viscometer, plate/plate system, plate diameter 10 mm, at a shear gradient of $2.62\ s^{-1}$ and 20° C. and the agent is so sticky that it can serve to attach bar-shaped agents to the toilet bowl or urinal, wherein the concentration of the surfactants in the case of an adhesion promoter from the group of polvalkyleneimines is between 7 and 60% by weight. The agent may have associated with it one or more bar-shaped compositions.

26 Claims, No Drawings

METHOD FOR CLEANING AND/OR DEODORIZING TOILET BOWL OR URINAL USING AN ADHESIVE AGENT

The present application is a continuation-in-part of U.S. patent application Ser. No. 12/735,987, inventors Joachim Leipold et al., filed Aug. 30, 2010, which in turn is a 371 of PCT Application No. PCT/EP2009/000873, filed Feb. 9, 2009, both of which are incorporated herein by reference.

The present invention relates to an adhesive agent for the sanitary sector, which serves in particular for application on a sanitary object such as a toilet bowl.

These agents are viscous, generally pasty agents, which are applied directly to the surface of the sanitary object from a suitable container, adhere there and can be flushed away only after a relatively large number of flushing operations.

WO 99/66017 discloses adhesive sanitary agents which serve for cleaning and deodorization and comprise surfactants, water, fragrances and adhesion promoters. Following direct application on the sanitary object, these sanitary agents are flushed away only after a relatively large number of flush cycles.

A further development of these adhesive sanitary agents with smoother surfaces as a consequence of additions of polyhydric alcohols is disclosed in EP 1 325 103 B1.

Further adhesive sanitary agents based on block copolymers comprising oligo- or polyalkylene oxides or on aryl ethoxylates or alkyl aryl ethoxylates as adhesion promoters are described in EP 1 318 191 B1 and adhesive sanitary agents containing bleaches are described in DE 10 2004 056 554 A1.

The known adhesive sanitary agents can be applied in a simple and hygienic manner using a suitable device, they adhere to the surface of the sanitary object, retain their shape and are not flushed away in their entirety even under the effect of water, but only gradually dissolve completely after a large number of flushes.

The particular advantage of these adhesive sanitary agents consists in the fact that additional containers such as the so-called "WC cages", the use of which is perceived by the consumer as being unhygienic, particularly when replacing the sanitary agent and when cleaning the toilet, are avoided.

In the field of conventional bar-shaped toilet cleaning and deodorization agents which are used in WC cages in the toilet bowl, in recent years a large number of multiphase products has been supplied:

Thus, for example, agents with an additional bleach phase are described in WO 00/23558, agents with a cleaning agent shaped-body phase and a gel phase are described in EP 1 418 225 A1 and cleaning agent shaped bodies with one phase comprising water-soluble salts and one phase comprising water-insoluble salts are described in WO 00/58434.

As a result of dividing the various functions to be fulfilled by a toilet cleaning and deodorization agent between several phases, for example a specific phase for intense deodorization and a special phase exclusively for cleaning, such multiphase agents are able to better meet the requirements of the consumer.

The object of the present invention is to provide a sanitary agent which can be applied in a simple and hygienic manner, which can be used in diverse ways and which fulfils consumer wishes with regard to intense deodorization and good cleaning.

This object is achieved by an agent for the sanitary sector, which agent can be applied directly on the sanitary object, adheres there and can be flushed away only after a relatively large number of flushing operations, where the agent comprises fillers from the group of surfactants and also an adhesion promoter, characterized in that the adhesion promoter is selected from the group of polyalkylene derivatives which comprise polyalkylene chains with randomly distributed functional groups, or from the group of copolymers from the group of monoalkylesters of poly/methyl vinylethers/carboxylic anhydrides, olefin homopolymers and copolymers of two or more olefins being partially oxidized or further functionalized via graft molecules, and from the group of polyalkyleneimines, also in alkoxylated form, polyether amines (alkoxylated amines) and polyglycerol polyether alkylcarboxylic acids or polymers or derivatives containing these polymer groups and the viscosity of the agent is at least 30 Pas, measured using a Haake viscometer, plate/plate system, plate diameter 10 mm, at a shear gradient of 2.62 $s^{-1}$ and 20° C. and the agent is so sticky that it can serve to attach bar-shaped agents in the toilet bowl, wherein the concentration of the surfactants in the case of an adhesion promoter from the group of polyalkyleneimines is between 7 and 60% by weight.

Surprisingly, it has been established that an agent with a viscosity of at least 30 Pas, measured using a Haake viscometer, plate/plate system, plate diameter 10 mm, at a shear gradient of 2.62 $s^{-1}$ and 20° C., which comprises fillers and also an adhesion promoter, where the adhesion promoter is selected from the group of polyalkylene derivatives, silicone systems, copolymers from the group of monoalkyl esters of poly(methyl vinyl ethers/carboxylic anhydrides, olefin homopolymers and copolymers of two or more olefins, being partially oxidized or further functionalized via graft molecules, and polyalkyleneimines, also in alkoxylated form, polyether amines (alkoxylated amines) and polyglycerol polyether alkylcarboxylic acids (esters of alkoxylated polyglycerols) or polymers or derivatives of these compounds containing these polymer groups, can be applied not only directly on the sanitary object, adheres there and can be flushed away only after a relatively large number of flushing operations, but, as a consequence of its stickiness, can also serve to attach bar-shaped agents to the toilet bowl.

The special adhesion promoters mean that the agent adheres to the sanitary surface and that further materials such as bar-shaped agents, for example with cleaning or deodorizing active ingredients, can be stuck to the surface of the adhesive. Moreover, these adhesion promoters are characterized in that the agents comprising these adhesion promoters can be flushed away without residue and that the agents comprising these adhesion promoters are insensitive towards fluctuations in the mixing ratio of adhesion promoter to filler.

By adding suitable fillers it is possible, for example, to adjust the viscosity and/or the flushability of the agent and to achieve the desired deodorization or coloring of the agent.

A broader field of use is opened up by the agent according to the invention:

In the case of the use of a water-soluble adhesion promoter, the agent can firstly be used as a water-soluble, temporarily adhering adhesive for attaching bar-shaped cleaning agents, e.g. in the form of extruded shaped bodies, in the toilet bowl, meaning that no special holding devices are required for these cleaning agents.

In this application of the agent as "pure adhesive", the agent serves as replacement for the WC cages perceived as unhygienic by the consumer. On the adhesive applied to the toilet bowl surface it is possible to attach bar-shaped agents comprising active ingredients having their own functionalities such as conventional rim blocks with one or more phases, rim blocks with scented phase, deodorization tablets, rim blocks containing bleach etc., where the adhesive replaces the WC cage in an hygienic manner and is gradually flushed away by the stream of flush water together with the bar-shaped agent adhering thereto. It is of course also possible for tablets compacted from powders or granules or else water-soluble or water-insoluble plastics containing active ingredients to be attached to the adhesive.

In this application, the agent has at least one of the adhesion promoters according to the invention and a thickener. Since the adhesion promoters according to the invention are generally viscous liquids, the addition of a thickener as filler is required so that the agent has the desired high viscosity of at least 30 Pas. Since the adhesion promoters according to the invention are water-soluble, in this embodiment, the addition of surfactants for increasing the ability to be flushed away is not required.

Further constituents such as dyes, fragrances, optionally surfactants, foamers etc. can of course also be added to this basic formulation of adhesion promoter and thickener.

In one modification of the first embodiment, besides the adhesion promoter and the thickener, the agent also has perfume so that it can be used simultaneously for adhesion and for deodorization.

In the second application, the adhesive has the adhesion promoters according to the invention and, as filler, surfactants, meaning that it can itself take on the cleaning function as a result of the suitable selection of the type and concentration of the surfactants and optionally further additives. The adhesive effect facilitates the fixing of further desired active ingredients in the toilet bowl, e.g. of a fragrance, of a bleaching tablet, of a descaling tablet, of an advertizing medium etc.

With the cleaning adhesive, the consumer can thus, for example, select a scent corresponding to his current wishes and press the corresponding deodorization tablet onto the applied cleaning adhesive such that it sticks firmly to the adhesive, for example in order to deodorize the toilet for the next 1 or 2 weeks.

The adhesive according to the invention thus even makes it possible to offer the adhesive together with a series of deodorization tablets or deodorization gels, bleaching tablets, descaling tablets, intensive cleaning tablets etc. in a combined set and thus to make it possible for the user to individually equip the adhesive.

If the consumer would like additional bleaching, then, for example, a bleaching tablet is stuck onto the surface of the adhesive.

If the consumer would like particularly powerful and intensive cleaning of the toilet, then another cleaning tablet can additionally be stuck onto the cleaning adhesive. The build-up of multilayered agents consisting of the layers adhesive-functionality-adhesive-functionality is also possible.

In contrast to this, although the agents known hitherto and described at the start exhibit a good and lasting adhesion on the sanitary object, a "sticking on" of another agent is not possible with the adhesive sanitary agents known hitherto.

Besides use in the field of toilet hygiene, the agent can also be used as cold adhesive which, as a result of the added surfactants, can be flushed away with water. The agent can be used as cold adhesive in the sanitary sector, e.g. for the attachment of objects in urinals, but also in handwashing basins or on tiles in the shower, or else in kitchens, restaurants, slaughter houses or other places where water is used for rinsing.

By using the cold adhesive in places where water is used for rinsing, at the same time as rinsing away the adhesive, cleaning also takes place as a result of the surfactants present in the adhesive.

Likewise conceivable is the use of the agent according to the invention in washing facilities for the cleaning of motor vehicles or for application on/in drains or gullies, for example in order to temporarily deodorize these.

The agent according to the invention can also be used as a wash-off paste for accommodating bait to combat vermin or for attachment to windows or facades which are rained on, so that the agent is consumed gradually.

The individual constituents of the agent according to the invention are described below:

A preferred class of the non-water-soluble adhesion promoters from the group of polyalkylene derivatives includes polyalkylene chains with randomly distributed functional groups. The polyalkylene chains are preferably polybutadiene, polyisopropylene and polypropylene chains.

The functional groups randomly distributed over the polyalkylene chains are preferably reactive groups, in particular from the group of anhydrides, thiols, epoxides or primary amines.

Particular preference is given to polymers with maleic anhydride groups bonded randomly to the polybutadiene chain. The particularly preferred maleic anhydride adduct onto 1,4-cis-polybutadiene is available from Degussa under the name Polyvest.

Furthermore, as non-water-soluble adhesion promoters it is possible to use silicone systems, for example from the group of construction silicones eliminating acetic acid (acetate system).

Such organopolysiloxane mixtures also known as cold-vulcanizing, single-component silicone rubbers, usually crosslink at room temperature with absorption of water from the surrounding atmosphere to give rubber-elastic polymers. The chain extenders and crosslinkers used are di- and preferably polyfunctional acetoxysilane compounds which eliminate acetic acid as a result of reaction with the polysiloxane or as a result of hydrolysis and thus initiate the formation of a macromolecular network.

Of suitability in principle as adhesion promoters are, however, also the silicone systems based on amine/aminoxy systems, oxime systems, benzamide systems and alkoxy systems, provided these can be stabilized with the additional system components described hereinbelow to give homogeneous, stable mixtures.

Furthermore, olefin homopolymers and copolymers of two and more olefins which, are partly oxidized or further functionalized via graft molecules can be used as adhesion promoters. These compounds include, for example, the polybutadiene rubbers, the styrene-butadiene block polymers and copolymers, and the polyisopropenes if they are partly oxidized or further functionalized via graft molecules. It is also possible to use the "random (block) polymers" which are prepared by 1,3-addition of butadiene or isoprene onto styrene or alpha-methylstyrene, the homopolymers or copolymers of ethylene and propylene, such as the ethylene-propylenediene terpolymers, ethylene-ethylene oxide copolymers, natural rubber and norbornene polymers such as polydicyclopentadiene if they are partly oxidized or further functionalized via graft molecules.

As water-soluble adhesion promoters it is also possible to use copolymers from the group of monoalkyl esters of poly (methyl vinyl ethers/carboxylic anhydrides, which are commercially available, for example, under the trade name Gantrez from ISP.

A further preferred class of the water-soluble adhesion promoters are the polyalkyleneimines, i.e. polymeric amines or polymers which comprises polyimine groups.

The class of polyimines includes in particular the homopolymeric polyalkyleneimines of the general formula —$(R-NH)_{n-}$ where R=alkyl or alkyl derivative, n=$10\text{-}10^5$ and two- or three-dimensional crosslinking via the nitrogen function, depending on the degree of alkylation or arylation on the nitrogen.

A preferred class of the polyalkyleneimines are the polymeric spherical polyalkyleneimines which are based in particular on homopolymeric polyethylene with a certain ratio between primary, secondary and tertiary amine functions. These polyethyleneimines can quaternize with water or acids, i.e. form polycations.

Of course, besides the ethylene group, the polyalkyleneimines can also contain methylene, propylene, butylene or higher alkylene groups as alkylene group.

Polyalkyleneimines are available for example from BASF under the trade name Lupasol with different molecular masses and degrees of crosslinking.

In principle, the polyalkyleneimines can also be present in derivatized form and/or as cationic polymers.

Polyalkyleneimines are soluble in water and other polar solvents.

Similarly, these polyimines can also be used in alkoxylated, in particular ethoxylated or propoxylated, form.

Likewise suitable as adhesion promoters are the so-called polyether amines (alkoxylated amines), which are likewise water-soluble.

These are in particular ethoxylated or propoxylated primary and/or secondary and/or tertiary alkyl- or arylamines. The alkyl or aryl radical may be branched such that then (formally) di-, tri- or oligo- or poly(EO/PO)-amines are formed. The alkoxylated polyamines enter into typical amine reactions with other functional groups (amide formation, urea analogs, imine formation with carbonyls etc.).

Preferably the alkoxylated polyamines are selected from the group of polyether amines. The polyether amines may include tri-, bi- and/or monofunctional primary amines and, as polyether groups, polyethylene oxide groups, mixed poly(ethylene oxide/propylene oxide) groups or polypropylene oxide groups, the hydrophilicity of the polyether amines decreasing in this sequence. However, it is of course also possible for the alkoxylated amines to have other polyether groups, such as, for example, polybutylene oxide groups.

Polyether amines with diamines or polyether amines with secondary amines can likewise be used.

Polyether amines are available for example from Huntsman, USA under the trade name Jeffamine® T-5000.

The molar masses of the polyether amines can vary over a wide range. Within the context of the present invention, in particular polyether amines with molar masses between 500 and 5000 have been used.

On account of the comparatively low viscosity of the alkoxylated amines, it is necessary to add viscosity-increasing substances, such as, for example, pulverulent surfactants, polysaccharides (wood flour, starch, meal) lignin etc., as fillers, to the agents according to the invention.

Furthermore, derivatives of the polyimines which can be used are also the ethoxylated polyimines according to the formula below, i.e. the systems which are obtainable by ethoxylation of the polyimines:

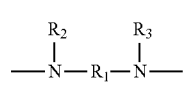 (1)

where $R_1$=alkyl or alkyl derivatives;
$R_2, R_3 = (-CH_2-CH_2-O)_n-R_4$ or $(-(CH_2)_3-O)_n-R_4$
$R_4$=H, alkyl, aryl; n=1-100

Derivatives of the polyimines which can likewise be used are compounds which are obtainable by reaction at the nitrogen function, such as, for example, polyurethane derivatives etc., i.e.
$R_2, R_3 = C(O)-N-X$
where X=copolymer, e.g. polyurethane, i.e. the side radical attaches again to a polymeric chain (imine quasi as copolymer of a block polymer) in the above formula (1).

Furthermore, according to the invention, polyglycerol polyether alkylcarboxylic acids can also be used as water-soluble adhesion promoters. These are polyether alkylcarboxylic acids which are esterified via glycerol, such as, for example, polyethylene glycol-150 polyglyceryl-2 tristearate or PEG-150 diglyceryl tristearate or PEG-150 tetraglyceryl distearate, where PEG-150 polyglyceryl-2 tristearate is preferred.

The polymer consists of a polyglyceryl backbone to which fatty acid radicals are attached via flexible PEG chains.

The thickening effect is presumably based on an associative interaction of the fatty acid radicals of PEG-150 polyglyceryl-2 tristearate with the surfactant micelles in the formulation. As a result of physical interaction, a 3-dimensional network could be spread out, which leads to the increase in viscosity in the aqueous surfactant system (for example a flushing operation in the toilet). The structure of the polymer, i.e. the polarity of the fatty acid ester (carbon chain length), the length of the flexible spacer (degree of ethoxylation of the PEG) and the structure of the backbone (number of glycerol units) have an influence on the thickening properties.

It is of course also possible to use combinations of the aforementioned adhesion promoters in the agent according to the invention.

As regards the selection of the adhesion promoters, their reactivity should also be taken into consideration. Within the context of the present invention, no particularly reactive polymeric starting compounds, such as, for example, reactive silicone masses, should be used as adhesion promoters since these always polymerize further and as a result always become more viscous. Also, systems based on polyurethane or with epoxide-containing starting compounds react too rapidly and become viscoelastic upon mixing. These systems adhere only slightly or no longer at all.

The adhesion promoter brings about the adhesion of the agent to the surface of the sanitary object. The agents according to the invention adhere both to dry surfaces and also to damp surfaces.

Furthermore, the special adhesion promoters also lead to the applied agent being sticky on its surface, such that other active ingredient agents can be stuck onto the surface of the adhesive.

In general, the adhesion promoter also forms network-like structures which impart the required dimensional stability to the agent even under the effect of strong force as a result of flushing water.

The concentration of the adhesion promoter to be used is dependent on the particular substance class and the ability of the adhesion promoter to form a network and is generally between 2% by weight and 60% by weight, preferably between 7% by weight and 50% by weight and particularly preferably between 8% by weight and 40% by weight.

Furthermore, the agent according to the invention comprises fillers, which can be selected from the group of surfactants, thickeners, fragrances, dyes, salts, foam stabilizers, foam boosters, foam generators and polymeric natural substances.

In principle, surfactants which can be used are all known anionic and/or cationic and/or nonionic and/or amphoteric surfactants, preference being given to pulverulent to highly pasty ones. The surfactant fraction in the agent should be between 0% by weight and 80% by weight, preferably 10% by weight to 60% by weight and particularly preferably 25% by weight to 45% by weight.

The anionic surfactants take on several tasks in the present invention; firstly, they serve, in the case of polymeric water-insoluble matrices, to emulsify the polymeric matrix without completely destroying the adhesiveness. Secondly, they make a significant contribution to the plastication of the starting polymer (adhesion promoter), by serving as viscosity increaser (thickener). Preferably, the anionic surfactants should also be highly-foaming in order to indicate visually a cleaning effect e.g. in a toilet bowl. Last but not least, a good cleaning effect of the surfactants is desired which is supported by the good wetting properties.

As anionic surfactants, preference is given to using one or more substances from the group of the salts of carboxylic acids, of sulfuric acid half-esters and of sulfonic acids, preferably from the group of fatty acids, fatty alkylsulfuric acids and alkylarylsulphonic acids. Usually, the carbon chain distributions of the anionic surfactants are in the range from 6 to 40, preferably 8 to 30 and in particular 12 to 22 carbon atoms.

Carboxylic acids (C6-C22) in the form of their metal salts (preferably alkali metal salts) and their natural or synthetic mixtures and also alkali metal salts of sulfuric acid half-esters and relatively long-chain alcohols can likewise be used as anionic surfactants.

A further class of anionic surfactants which can be used according to the invention are the alkali metal salts of alkyl ether sulfuric acids. Alkyl ether sulfuric acids are, like alkylsulfuric acids, synthesized from fatty alcohols, which are reacted with ethylene oxide to give the fatty alcohol ethoxylates in question. Instead of ethylene oxide, it is also possible to use propylene oxide. The subsequent sulfonation produces the alkyl ether sulfuric acids in question.

The alkali metal salts of alkanesulfonic acids and olefinsulfonic acids can also be used as anionic surfactants within the context of the present invention. Alkanesulfonic acids can contain the sulfonic acid group in terminally bonded form (primary alkanesulfonic acids) or along the carbon chain (secondary alkanesulfonic acids). Typical representatives are alkylbenzenesulfonates, particularly preferably linear alkylbenzenesulfonates (LAS).

The aforementioned anionic surfactants can be used in their neutralized form alone or in a mixture with one another.

According to the invention, the surfactant phase comprises, based on its weight, preferably 10 to 90 and particularly preferably 40 to 85% by weight of lauryl sulfate.

In adhesives with the thin-liquid adhesion promoter based on butadiene derivative, the anionic surfactants simultaneously also serve as thickeners.

Nonionic surfactants which can be used are alkoxylated, preferably ethoxylated, in particular primary alcohols having preferably 8 to 18 carbon atoms and on average 1 to 12 mol of ethylene oxide (EO) per mole of alcohol, in which the alcohol radical may be linear or preferably 2-methyl-branched or can contain linear and methyl-branched radicals in a mixture, as are usually present in oxo alcohol radicals. In particular, however, alcohol ethoxylates with linear radicals from alcohols of native origin having 12 to 18 carbon atoms, e.g. from coconut alcohol, palm alcohol, tallow fatty alcohol or oleyl alcohol and on average 2 to 8 EO per mole of alcohol are preferred. In addition to these nonionic surfactants, fatty alcohols with more than 12 EO can also be used. Examples thereof are tallow fatty alcohol with 14 EO, 25 EO, 30 EO or 40 EO.

Moreover, further nonionic surfactants which can be used are also alkyl glycosides of the general formula alkyl-O(G), where alkyl is a primary straight-chain or methyl-branched, in particular 2-methyl-branched, aliphatic radical having 8 to 22, preferably 12 to 18, carbon atoms, and G is the symbol for a glycoside unit having 5 or 6 carbon atoms, preferably glucose.

A further class of preferably used nonionic surfactants, which are used either as the sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters. Nonionic surfactants of the amine oxide type, for example N-cocoalkyl-N,N-dimethylamine oxide and N-tallow-alkyl-N,N-dihydroxyethylamine oxide or alkanolamides can also be used.

The fraction of the nonionic surfactant(s) in the overall surfactant phase can be up to 50%, preferably up to 30% and particularly preferably up to 25%.

The surfactant phase can, if desired, also be equipped with cationic or amphoteric and zwitterionic surfactants. Examples of amphoteric surfactants are fatty acid amidopropylbetaines with C5-C21 fatty acid fractions, but also amphodiacetates.

Cationic surfactants are preferably used in acidic formulations in combination with bactericidal substances. Zwitterionic surfactants can be described by way of example as quaternary ammonium, phosphonium or sulfonium components which are joined, via an aliphatic bridge, to a further now anionic group such as carboxy, sulfonate, sulfate, phosphate or phosphonate.

Furthermore, olefinsulfonates, ether sulfates or acid methyl taurides can be added as foamers to the agent. If strong foamers are to be used, then preferably 1 to 50, in particular 1-25% of the surfactant phase can be replaced by one or more foamers, e.g. from the group of betaines, alkoxylated alkyl ether sulfates or lactobionic acid derivatives. These foamers can be selected from the fatty acid amidopropylbetaines with a C5-C21-fatty acid fraction such as, for example, cocoamidopropylbetaine, the alkali metal or ammonium salts of lauryl ether sulfates with 1 to 5 EO, lacto-bionococoylamide, lactobionooleylamide, lactobiono-talgamide etc. or mixture thereof. These foamers can be incorporated easily into the pressure-sensitive adhesive. Preference is given to using those cosurfactants which are present in solid, preferably pulverulent or high-viscosity form.

Besides the constituents according to the invention, the adhesive can comprise further customary constituents, for example salts, disinfectants (e.g. oxygen or chlorine donors), preservatives, such as, for example, isothiazolone derivatives, foam stabilizers such as, for example, alkanolamides, hydrophobicizing agents such as, for example, mineral oils or (partially) methylated siloxanes and silanes, calcium dispersants such as sodium salts of polycarboxylic acids or dyes.

By adding perfume oil or fragrances, the adhesive can also be used for deodorizing the air.

Perfume oils and fragrances which can be used are individual odorant compounds, e.g. the synthetic products of the aldehydes, alcohols, esters, ethers, ketones and hydrocarbons. Odorant compounds of the ester type are e.g. benzyl acetate or benzyl formate. The ethers include, for example, benzyl ethyl ether, the aldehydes include e.g. citronellal, the ketones include α-isomethylionone, the alcohols include citronellol, eugenol, geraniol and linalool. The hydrocarbons include primarily the terpenes such as limonene and pinene. However, preference is given to using mixtures of different fragrances which together produce the desired scent note. These also include those perfume oils which comprise natural odorant mixtures, as are accessible from vegetable sources, such as e.g. pine oil, citrus oil, lavender oil, mint oil or oil from orange peel.

The fragrances are incorporated directly into the batch in concentrations between 0.25% by weight and 20%, preferably between 3% by weight and 15% by weight and particularly preferably between 5% by weight and 10% by weight.

If desired, salts such as, for example, sodium sulfate can also be added to the formulation as fillers, for example in order to increase the dissolution rate. In the case of particularly cost-effective product, the salt fraction can be up to 90% by weight. In general, the salt fraction is up to 10% by weight, preferably up to 5% by weight. Suitable salts are alkali metal salts of strong acids, such as sodium sulfate, sodium chloride or else sodium polyphosphate. It is likewise possible to use the alkali metal salts of the mono-, di- and polycarboxylic acids, but also alkaline earth metal salts of strong acids, such as calcium sulfate or salts of carbonic acid.

Calcium salts can be used in particular for increasing the service lives of the agent since they form, for example with the maleic anhydrides of the adhesion promoters based on polybutadiene derivative, polysoaps which in turn have a hydrophobicizing effect and stabilize the entire system with the formation of calcium soap networks on the surface and thus counteract an ability to be flushed away.

In the event of excessive hydrophobicization of the agent through the formation of calcium polysoaps, in order to increase the ability to be flushed away, calcium soap dispersants, such as e.g. ampho-dipropionates (Lonza KL grade) or maleic acid/acrylic acid copolymer Na salts (BASF Sokalan grades such as Sokalan CP5 or CP45) can be added to the agent.

Moreover, all dyes which do not have marked substantivity towards the surfaces to be treated with the dye-containing agents can be incorporated as fillers into the agent. If water-soluble dyes are used in the formulation and the latter then comes into contact with water as a finished product, e.g. upon flushing with water in a toilet bowl, interesting color progressions can be achieved which can also be correlated with marketing arguments. For example, a slow blue coloration (from pale blue to deep blue) can indicate the slow activation of an active ingredient up to its maximum activity.

Similarly, the adhesive can also be rendered acidic and comprise, for example, substances which dissolve lime scale or urine scale (acids) as fillers.

Furthermore, (co)thickeners can be added to the agent according to the invention in order to increase the plasticity of the agent. (Co)thickeners which can be used are, for example, bentonites, powder surfactants, xanthans, polybutadiene rubbers, polyisopropenes, block copolymers, which contain linked oligomers consisting of oligo- or polyethylene oxide and/or oligo- or propylene oxide and/or oligo- or polybutylene oxide, and also aryl ethoxylates or alkyl-aryl ethoxylates. The polymeric natural substances such as the lignins or their alkali metal or alkaline earth metal salts can also be used as (co)thickeners.

One preferred group of (co)thickeners is the hydrophilic xanthans. Through their use, a very hydrophilic compound is introduced into the agent which, upon sticking the agent onto a damp surface, immediately "sucks up" the water.

Furthermore, hydrophobicizing agents such as, for example, Aerosil, in particular thoroughly methylated Aerosil (Carbot Carbon) can be added as fillers to the adhesive.

If an increase in the rate of adhesion should be desired, so-called tackifiers, in particular from the class of hydrocarbon resins, natural resins such as tall resin or balsam resin, or polyterpene resins, can also be added as fillers to the agent.

In order to counteract unpleasant odors, the adhesive can also comprise malodor counteractants, which are preferably added to the fragrances. Such malodor counteractants are described, for example, in U.S. Pat. No. 7,288,507 B2.

The adhesive according to the invention can be applied and replaced in a hygienic manner without touching possibly contaminated devices attached to the WC bowl.

An essential advantage of the agent according to the invention is that it can be portioned as the consumer desires and/or can be supplied in different portion packs. The adhesive can be applied for example by means of an application syringe or by application of preportioned amounts by means of suitable devices. These application devices may be for example "clip systems", grippers or small plates removable from films, dispenser systems with pretensioned elements which fire a corresponding portion e.g. onto a ceramic surface.

The agent according to the invention can also be applied in a simple manner at the same time to different places on the sanitary object, for example in order to stick on two or more active ingredients which, in direct vicinity, would adversely affect one another in their effect, such as, for example, a deodorizing tablet and a bleaching tablet.

The achieved adhesion to the sanitary object, even in the case of application to a vertical surface, is so good that the agent does not come off even under the additional action of force of streams of flush water.

The adhesives according to the invention can only be flushed away after a relatively large number of flushing operations. The number of flushing operations is naturally governed by the composition of the particular agent, the amount applied and the geometry of the applied agent and is generally, for an application with a thickness of 2 to 5 mm, between 50 and 150, in particular more than 120, flushes.

If the agent is used as adhesive in the toilet bowl, the durability is essentially defined via the flush-away time of the applied further body (bar-shaped agent). In the case of a conventional toilet block, thus a service time of from 100 to 200, in many cases >250 flushes, can be achieved, the adhesive agent being gradually washed away together with the stuck-on material. The applied amount is 3 to 15% by weight, in particular 5 to 10% by weight, of the mass of the stuck-on agent.

Preferably, the agent according to the invention is white, ointment-like, pasty and/or cream-like and dimensionally stable so that it does not "run off" or "drip".

The adhesion and also the shape of the agents is retained despite the considerable forces (friction, deformation, shear effect) which act as a result of the water flushing.

The agent essentially exhibits pseudoplasticity, i.e. the viscosity decreases with increasing shear forces.

If the shear rates are low, however, a severe flow constraint is observed; moreover, the viscosity curves at a shear rate ramp between $2.5\ s^{-1}$ and $30\ s^{-1}$ show the appearance of local maxima. There are evidently areas of differing viscosity or the agent changes its structure over the short measurement time (ramp time 100 sec).

The viscosities of these agents, to be determined using a Haake viscometer, plate/plate system, plate diameter 10 mm at a shear gradient of $2.62\ s^{-1}$ and $20°\ C.$, should be at least 30 Pas, preferably at least 45 and particularly preferably at least 100 Pas. Preferably, the viscosities should be between 150 or 300 and 6000 Pas and particularly preferably between 200 and 1000 or between 1000 and 4000 Pas.

Preferably, the agents according to the invention which comprise surfactants produce a finely-bubbled foam which can be adjusted in respect of its volume by suitable additives (foam boosters). The foam numbers of the agents according to the invention should be more than 40 ml of foam. Particular preference is given to agents with foam numbers of >60 ml, very particular preference being given to foam numbers of 140 ml or even more than 200 ml.

The surface tension of the agents can be between 50 and 65 mN/m. Preference is given to those agents whose surface tension is $\leqq 60$ mN/m. Particular preference is given to agents which achieve surface tensions equal to or less than 40 mN/m. The surface tension is a measure of the wetting of the surface. The lower the surface tension, the better the surface is wetted. A good wetting effect is a prerequisite for a good cleaning performance of the agents under consideration.

The agent according to the invention is prepared by stirring the components together at room temperature.

The invention is described below by reference to various embodiments and experiments.

Table 1, which is attached at the end of the description, lists various formulations of the adhesives according to the invention.

The flush numbers in table 1 were determined on applied amounts of 2-5 g.

Table 2, which again is attached at the end of the description, lists the starting materials used for producing the agents according to the invention in table 1.

All of the adhesives of the invention according to formulations V13 to V38 exhibit strong adhesion and are so sticky on their outside that conventional toilet cleaning agents with a mass of up to 50 g can be stuck onto the agents depending on what amounts of adhesive are applied. The ratio of stuck-on mass of the bar-shaped agents to the adhesive mass here is at most 100:1, preferably at most 50:1 and particularly preferably at most 10:1. Better adhesion of the agent is naturally achieved if the adhesive surface is larger. The customary adhesive surfaces are between 1000 mm$^2$ and 800 mm$^2$ (full-area contact). However, they may also be less than 400 mm$^2$ if the adhesive is applied in the form of circular beads.

In all of the flushed-off experiments, the surfactants used were anionic surfactants. The flush numbers of these agents exhibit relatively high to high service lives.

V20 is a formulation for an acidic agent. The lower flush numbers of this agent are presumably due to the fact that, as a result of the low pH, no lime soaps (which increase the flush numbers) are formed.

Formulations V23a, V29 and V30 comprise only one (anionic) surfactant and an adhesion promoter. These agents consisting only of two components also exhibit the desired adhesion, the required stickiness and flush numbers of more than 100.

Compared to this, the applied pure adhesion promoter Polyvest 800 S (1,4-cis-butadiene maleic anhydride adduct), a thin-liquid product, immediately runs down on the toilet bowl and exhibits no adhesion. Sticking on a customary toilet block of 50 g, 30 g, 10 g, 5 g is not possible on the pure adhesion promoter Polyvest. The bar-shaped agent immediately falls down; no adhesive effects are observed.

Table 3, which is likewise attached at the end of the description, summarizes the results of various adhesion experiments carried out using the agents of the invention according to table 1.

To carry out the adhesion experiments, either the stated defined amount of adhesive agent (adhesive) was coated onto the reverse of the sample body to be firmly attached through adhesion, or the adhesive was applied to one surface of the sample body using a spatula to a thickness of ca. 2-4 mm.

The sample body was then stuck directly into a ceramic toilet bowl. As a rule, the sample bodies were stuck to the damp front inside surface of the toilet using slight pressure. Adhesive agents and sample bodies are immediately ready for use and can be directly flushed over.

The experiments in table 3 demonstrate that the adhesive agents according to the invention containing the adhesion promoter Polyvest, the 1,4-cis-polybutadiene maleic anhydride adduct, not only adhere to the sanitary bowl, but also have such good adhesive properties that they are suitable for the sticking on of toilet blocks, descaling tablets, transparent soap systems etc. in the bowl.

Comparing the adhesion behavior of the systems of the present specification with the systems from WO 99/66017, it can be established that the latter enter into no kind of adhesive function with the sample bodies listed in table 3.

As soon as it is attempted e.g. to attach a customary toilet block to the surface of the gel from WO 99/66017, the latter immediately slips down on account of gravity. Consequently, no kind of durable adhesive functionalities are built up.

On the part of the applicant, it is assumed that the good adhesive properties of the present Polyvest-based agents are due firstly to the present randomly distributed maleic anhydride groups, which bring about a chemical adhesion with functional groups on the surface of the carrier (reactive adhesive); on the other hand, however, this effect might also continue inwards and the maleic anhydride groups react with functional groups in the structure (e.g. with the nucleophilic groups of the surfactants and cothickeners involved) (cohesion effect), such that more or less extended structures analogous to the glyptal resins are probably formed.

The starting substance in pure form is also already a pressure-sensitive adhesive which has lasting stickiness over a long period (until the reactive groups are cured). However, such a pure adhesive (without surface-active fractions) can only be removed from a ceramic surface with great difficulty, if at all.

The cohesion effect of the maleic anhydride function should increase e.g. in the case of long-chain fatty alcohols or in the case of long-chain PEG systems (e.g. Polyox WSR 303) which are also incorporated into the formulation.

A first indication of said interaction is given in experiment V22 in combination with the V2 block (table 3). The formulation of the V2 block produces flush numbers of more than 460 for a significantly smaller sample body.

In addition to the crosslinking processes, in the case of the present formulation, the formation of polysoaps from the calcium ions can also play a role, which leads to greater hydrophobicization of the entire system and thus to poorer solubility in water.

A further contribution to increasing the forces of adhesion is expected by the xanthan involved. The rapid formation of hydrocolloids upon contact with the aqueous surfaces in the toilet system results in rapid water removal on the surface. Consequently, other, e.g. adhesive, interactions of the adhesive with a pseudodry ceramic surface can rapidly be established.

As a consequence of these overall interactions, the adhesive compounds remain stuck to the surface of a ceramic object for a relatively long time, even if it is flushed over with water. This is all the more surprising since the water in the flushing operations ought to actually back-migrate the surfactant-containing agent (with good wetting numbers) and thus lead to detachment from the ceramic object.

In the present system, it is even the case that the adhesive mass or a second component stuck on therewith is eroded from the outside inwards.

Table 4, which is attached after the description, lists by way of example the foam numbers and surface tensions of a number of agents according to the invention from table 1.

Table 4 shows that the agents according to the invention differ significantly from the agents known hitherto from EP 1325103 B1. The present agents are thus significantly better foamers.

To determine the foam numbers, 100 ml of the stock solution thermostated at 20° C. are transferred to a 250 ml mixing cylinder, which is closed with a PTFE stopper. The cylinder is then moved to and fro twenty times (inverted 20 times). After in each case 30 sec/5 min/30 min, the generated foam volume (ml) is read off and noted.

The surface tensions were determined using the BP 2 instrument from Krüss bubble-pressure measuring instrument.

When checking the blank value, the procedure was as follows: using the Ufaryl DL 90 C a 0.1% strength solution is prepared, at 20° C. a measurement curve is recorded three times with the capillary diameter ascertained beforehand and averaged. The deviation from the average must be not more than 1 mN/m.

The first test is taken as initial value, all of the subsequent tests are compared with the initial value (50/100/500 ms). In the event of deviation greater than ±2 mN/m, the capillary is exchanged for a new one.

For the measurement, the surface tension of a 0.1% strength solution (20° C.) was ascertained as a function of the age of the surface. The surface tension after 100, 500, 1000 ms is observed here.

Table 5 lists various formulations of the adhesive agents according to the invention containing polyalkyleneimines as adhesion promoter, and table 6 lists alkoxylated amines and polyglycerol polyether alkylcarboxylic acids.

TABLE 5

| | Amount [g] | | | |
|---|---|---|---|---|
| | Sample No. 100 | Sample No. 101 | Sample No. 102 | Sample No. 103 |
| Tensopol USP 94 | 8.00 | 8.00 | 8.00 | 8.00 |
| Marlinat 242/90T | | 4.50 | | 4.50 |
| Orange Fun | 2.05 | 2.05 | 2.05 | 2.05 |
| Kelzan ASX | 0.16 | 0.16 | 0.16 | 0.16 |
| Sodium sulfate | | | 70.0 | |
| Lupasol SK | 5.92 | | | |
| Lupasol P | | 5.90 | | |
| Genapol DAT | | | 5.92 | 1.50 |
| Emanon XLF | | | 1.50 | 1.50 |
| Sum Initial weight | 16.13 | 16.11 | 92.13 | 17.71 |
| Percentage fraction of the adhesion promoter | 36.3 | 36.6 | 8.1 | 16.9 |
| Viscosity [Pa s] | 47 | 1906 | 710 | 317 |
| Foam value [30 s, 5 min, 30 min] | 100/90/60 | 125/110/90 | 80/60/40 | 160/140/130 |
| Bubble pressure [100, 500, 1000 ms] | 53/46/43 | 59/51/47 | 63/54/50 | 49/40/37 |
| Flush number upon application of the pure mass* | 1 | 95 | 160 | 57 |
| Flush number, application of the mass to block** | 12 | 128 | 180 | 120 |

TABLE 5-continued

| | Amount [g] | | | |
|---|---|---|---|---|
| | Sample No. 100 | Sample No. 101 | Sample No. 102 | Sample No. 103 |
| Adhesion base | dry and wet | dry and wet | wet | wet |

*application was carried out using an applicator with a narrow rectangular opening in a stripe of width ca. 2 cm and thickness ca. 3 mm.
**the agent was applied to a toilet block, the applied amount was ca. 10% of the weight of the toilet block. The toilet block was then stuck to the sanitary surface by the agent.
Tensopol USP 94 is a surfactant (C12-C16 lauryl sulfate), available from Manro.
Marlinat 242/90T consists of C12-C14-alcohol polyethylene glycol and propylene ether (2 EO) sulfate, glycol triisopropanolammonium salt (Sasol).
Orange Fun is a perfume, available from Givaudan.
Kelzan AS is a xanthan (thickener/cothickener), available from Kelco.
Genapol DAT is PEG-150 polyglyceryl-2 tristearate and PEG-6 capryl/capric glyceride.
Lupasol SK is a liquid polyethyleneimine with a molar mass of ca. 2000000 available from BASF, Lupasol P is a liquid polyethyleneimine with a molar mass of ca. 750000 available from BASF.

TABLE 6

| | Amount [g] | | | | | |
|---|---|---|---|---|---|---|
| | Sample No. 104 | Sample No. 105 | Sample No. 106 | Sample No. 107 | Sample No. 108 | Sample No. 109 |
| Tensopol USP 94 | 10 | 6 | 8 | 8.50 | 12.00 | 8.00 |
| Marlinat 242/90T | 4.80 | 4.50 | 4.50 | 2.25 | 4.50 | |
| Orange Fun | 2 | 2 | 2.05 | 2.05 | 2.05 | 2.0 |
| Kelzan ASX | 0.15 | 0.15 | 0.16 | 0.16 | 0.16 | 0.15 |
| Emanon XLF | 1.50 | 1.50 | 1.50 | 1.50 | 1.50 | |
| Jeffamine T 5000 | 6.00 | 6.00 | 5.94 | | | |
| Jeffamine ST-404 | | | | | 3.00 | 5.94 |
| Chalk (CaCO₃) | 2.50 | | | | | |
| Cab-Osil Arboform water-soluble | | 1.50 | | | | |
| Hydriol PGR | | | | | | 6.61 |
| Sum Initial weight | 26.95 | 21.65 | 22.15 | 17.46 | 26.15 | 16.76 |
| Percentage fraction of the adhesion promoter | 22.2 | 27.7 | 26.8 | 17.2 | 22.7 | 39.4 |
| Viscosity [Pa s] | 503.6 | 401 | 227 | 228 | 220 | 226 |
| Foam value [30 s, 5 min, 30 min] | | 170/165/150 | 130/120/50 | 210/180/160 | 200/175/150 | 45/10/5 |
| Bubble pressure [100, 500, 1000 ms] | | 52.6/43.9/41.1 | 50/42/40 | 43/35/33 | 43/35/33 | 57/48/45 |
| Flush number upon application of the pure mass* | 21 | 84 | 70 | 49 | 43 | 71 |

TABLE 6-continued

| | Amount [g] | | | | | |
|---|---|---|---|---|---|---|
| | Sample No. 104 | Sample No. 105 | Sample No. 106 | Sample No. 107 | Sample No. 108 | Sample No. 109 |
| Flush number, application of the mass to block** | 193 | 208 | 34 | 105 | 101 | 65 |
| Adhesion base | wet | wet | wet | wet | wet | dry wet |

Emanon XLF is glycereth-7 caprylate/caprate, available from KaO Corporation, S.A.
Jeffamine T 5000 is a polyether amine, available from Huntsman, USA, with a molar mass of ca. 5000 (triamine which is prepared by reaction of propylene oxide with a triol initiator, followed by an amination of the terminal hydroxy groups).
Jeffamine ST-404 is a modification of the polyether amines with a molecular mass of ca. 565, available from Huntsman, USA (secondary amine version, secondary triamine. The amine end groups are reacted with a ketone, e.g. acetone, and reduced).
Cab-Osil is a highly disperse silica.

Arboform, water-soluble, is available from Tecnaro, Ilsfeld, Germany and is granules which consist of the polymers lignin or lignin derivatives, biodegradable polyesters, lignocellulose or lignocellulosic fibers and natural resins, namely aliphatic and aromatic ketones, alcohols, carboxylic acids, lactones and polycycles in monomeric, oligomeric and polymeric form.

Hydriol® PGR is polyglycerol polyricinoleate.

All of the investigated agents according to the invention adhere/stick exceptionally both to dry and to wet surfaces.

Also, they are so sticky on their outside that conventional toilet cleaning agents with a mass of up to 50 g or even more can be stuck onto the agents, depending on what amounts of adhesive are applied. In all of the flushed-off experiments, the surfactants used were anionic surfactants. The flush numbers of these agents exhibit relatively high to high service lives.

The surface tensions were determined using the BP 2 instrument from Krüss bubble-pressure measuring instrument.

When checking the blank value, the procedure was as follows: using the Ufaryl DL 90 C a 0.1% strength solution is prepared, at 20° C. a measurement curve is recorded three times with the capillary diameter ascertained beforehand and averaged. The deviation from the average must be not more than 1 mN/m.

The first test is taken as initial value, all of the subsequent tests are compared with the initial value (50/100/500 ms). In the event of deviation greater than ±2 mN/m, the capillary is exchanged for a new one.

For the measurement, the surface tension of a 0.1% strength solution (20° C.) was ascertained as a function of the age of the surface. The surface tension after 100, 500, 1000 ms is observed here.

The flush numbers were measured using a flush volume per flush of 8 l and a flush rhythm of 19 flushes per day according to a defined scheme. The flush-water temperature during the short flush frequencies (for example between the third and fifth flush) was 13° C. to 14° C. and during the long resting periods (for example between the nineteenth and first flush) was 15° C. to 16° C. The temperature of the flush water was checked on each work day and noted.

TABLE 1

| | V13 in g | V14 in g | V15 in g | V17 in g | V19 in g | V19.1 in g | V20 in g | V22 in g | V23a in g | V29 in g | V30 in g | |
|---|---|---|---|---|---|---|---|---|---|---|---|---|
| Tensopol USP 94 | 15.72 | 48.7 | 47.59 | 39.09 | 38.4 | 37.37 | 42.55 | 40.72 | 69.75 | 20.39 | 29.67 | surfactant |
| Polyvest 800S | 37.80 | 38.22 | | 32.77 | 31.3 | 30.43 | 35.1 | 30.96 | 30.25 | 79.61 | 70.33 | adhesion promoter |
| Calcium sulfate (dihydrate) | | | | 17.19 | 14.9 | 16.87 | | | | | | salt |
| Bentonite | 32.26 | | | | | | | | 11.69 | | | thickener |
| Construction silicone | | | 39.44 | | | | | | | | | thickener |
| Kelzan ASX | 1.07 | 0.91 | 0.95 | 0.83 | 0.7 | 0.7 | 0.8 | 1.02 | | | | thickener |
| Aerosil TS 720 | | | | | 4.9 | 5.17 | 5.32 | 5.19 | | | | hydrophobicizing agent |
| Blue color | | | | | | 0.0001 | | | | | | color |
| Orange Fun | 13.14 | 12.2 | 12.02 | 10.13 | 9.7 | 9.41 | 10.64 | 10.42 | | | | perfume |
| Citric acid | | | | | | | | | 5.59 | | | acid |
| Total [in g] | 99.99 | 100.03 | 100.00 | 100.01 | 99.90 | 99.95 | 100.00 | 100 | 100 | 100.0 | 100.00 | |
| Flushes: | >400 | ca. 140 | no experiment | 120 | >130 | >250 | 72 | 94 | 168 | no experiment | no experiment | |

| | | V34 in g | V35 in g | V36 in g | V37 in g | V38 in g | |
|---|---|---|---|---|---|---|---|
| | Tensopol USP 94 | 36.99 | 37.22 | 37.08 | 36.90 | 37.13 | surfactant |
| | Polyvest 800S | 36.99 | 36.97 | 37.08 | 37.08 | 37.13 | adhesion promoter |
| | Calcium sulfate (dihydrate) | | | | | | salt |
| | NaCl | | | | 12.30 | | salt |
| | Sodium sulfate | | | | | 12.32 | salt |

TABLE 1-continued

|  |  |  |  |  |  |  |
|---|---|---|---|---|---|---|
| Bentonite |  |  |  |  |  | thickener |
| Construction silicone |  |  |  |  |  | thickener |
| Kelzan ASX | 0.99 | 0.99 | 0.93 | 1.05 | 0.92 | thickener |
| Aerosil TS 720 |  |  |  |  |  | hydrophobicizing agent |
| Blue color |  |  |  |  |  | color |
| Orange Fun | 12.45 | 12.51 | 12.55 | 12.67 | 12.50 | perfume |
| Citric acid |  |  |  |  |  | acid |
| Nonionic surfactant | 12.58 |  |  |  |  | surfactant |
| Betaine |  | 12.32 |  |  |  | surfactant |
| Anionic surfactant |  |  | 12.36 |  |  | surfactant |
| Total [in g] | 100.00 | 100.01 | 100.00 | 100.00 | 100.00 |  |
| Flushes: | no experiment | no experiment | no experiment | no experiment | no experiment |  |

TABLE 2

|  | Manufacturer | Grade | Chemistry | Function |
|---|---|---|---|---|
| Bentonite | Süd-Chemie | Optigel CL | Bentonite | thickener |
| Tensopol USP 94 | Manro | Tensopol USP 94 | C12-C16 lauryl sulfate | surfactant |
| Orange Fun | Quest | # F561415 |  | perfume |
| Construction silicone | Sales: Meister Werkzeuge/Werkzeugfabrik Wuppertal, Wuppertal |  |  | thickener |
| Aerosil TS 720 | Carbot Carbon | TS 720 |  | hydrophobicizing agent |
| Kelzan ASX | Kelco | Kelzan ASX | Xanthan | Thickener/cothickener |
| Polyvest 800S | Degussa | Polyvest 800S | 1,4-cis polybutadiene, maleic anhydride adduct | adhesion promoter |
| Calcium sulfate (dihydrate) | Krone-Gips |  |  | filler |
| Blue color |  |  |  |  |
| Citric acid | Jungbunzlauer |  |  | acid |
| Nonionic surfactant | Kolb | Imbentin AG/168S300SP | Fatty alcohol (30 EO) | surfactant |
| Betaine | Goldschmidt | Tego Betain CKD | Cocamidopropylbetaine | surfactant |
| Anionic surfactant | Sasol | Marlon ARL | Alkylbenzenesulfonate, Na salt | surfactant |
| NaCl | Solvay |  |  | salt |
| $Na_2SO_4$ | Merck |  |  | salt |

TABLE 3

|  | Flush No. | Notes |
|---|---|---|
| Adhesive material from experiment No. 22 |  |  |
| 1 V2 block with Polyox<br>initial weight of block: 2.46 g<br>initial weight of adhesive: 0.4 g | 467 | The V2 block consisted of 32% by wt. of anionic surfactant, 6% by wt. of sodium cumenesulfonate, 43% by wt. of filler, 10.5% by wt. of calcium sulfate, 0.5% by wt of Polyox WSR 303 resin (Union Carbide), 2% by wt of polyethylene glycol and 6% by wt. of perfume |
| 2 Standard 2 in 1 block<br>initial weight of block: 30.92 g<br>initial weight of adhesive: 3.37 g | 530 | According to EP 1418225 B1, the extruded phase is the contact phase |
| 3 Standard yellow formulation<br>initial weight of block: 11.13 g<br>initial weight of adhesive: 2.41 g | 378 | According to EP 0844303 B1 |
| 4 Standard 2 in 1 block (bouquet)<br>initial weight of block: 44.75 g<br>initial weight of adhesive: 1.28 g | 90 | According to EP 1418225 B1; other embodiment; the gel phase is the contact phase; |
| Adhesive material from experiment No. 19 |  |  |
| 5 Transparent soap | 268 | according to DE 102007005617.8 |
| Adhesive material from experiment No. 20 |  |  |
| 6 PP cage stuck into bowl | 25 | Standard commercial PP toilet cage |
| 7 Descaling tablet | 7 | Formulation according to DE 10333905 A1. The block produces $CO_2$ with water and is therefore effervesced off from the surface. |

TABLE 4

| Experiment number | Foam number [mm] | [Pas], PP, 10 mm, 20° C., γ' = 2.62 s⁻¹ | [Pas], Senior PK 5, 20° C., ¹γ' = 0.3 s⁻¹ | Surface tension |
|---|---|---|---|---|
| 13 | foam (ml); (0.1%); 30 sec/5 min/30 min | n.d. (not determined) | 919 | Surface tension [mN/m]; (0.1%); 100 ms/500 ms/1000 ms |
| 14 | 60/8/4 | 415 | not measurable | 64.6/56.9/53.3 |
| 19 | 40/20/10 | 2263 | not measurable | 55.9/47/44.2 |
| 23 | 40/12/3 | 5965 | not measurable | 60/51/47.4 |
| 31 | n.d. | 3382 | not measurable | n.d. |
| Comparison gel from EP 1325103 B1 | 70/25/10 | 524 | n.d. | 56.6/48.7/45.5 |

What is claimed is:

1. A method for cleaning and/or deodorizing a toilet bowl or urinal comprising directly applying an agent to the toilet bowl or urinal, wherein the agent adheres to the toilet bowl or urinal and can be flushed away only after a relatively large number of flushing operations, wherein the agent comprises fillers from the group of surfactants and also an adhesion promoter, wherein the adhesion promoter is selected from the group of polyalkylene derivatives which comprise polyalkylene chains with randomly distributed functional groups, or from the group of copolymers from the group of monoalkylesters of poly/methyl vinylethers/carboxylic anhydrides, olefin homopolymers and copolymers of two or more olefins being partially oxidized or further functionalized via graft molecules, and from the group of polyalkyleneimines, alkoxylated polyalkyleneimines, polyether amines or alkoxylated amines and polyglycerol polyether alkylcarboxylic acids or polymers or derivatives containing these polymer groups, wherein the viscosity of the agent is at least 30 Pas measured using a Haake viscometer, plate/plate system, plate diameter 10 mm, at a shear gradient of 2.62 s⁻¹ and 20° C. and the agent is so sticky that it can serve to attach bar-shaped agents to the toilet bowl or urinal, wherein the concentration of the surfactants is between 10 and 80% by weight, and wherein the agent has associated therewith one or more bar-shaped compositions selected from the group consisting of conventional rim blocks with one or more phases, rim blocks with scented phase, rim blocks containing bleach, compacted tablets, deodorization tablets, solid deodorization gels, bleaching tablets, descaling tablets or intensive cleaning tablets.

2. A method for adhering an object to a toilet bowl or urinal, the method comprising directly applying an agent as cold adhesive to the toilet bowl or urinal, the object being associated with the agent, wherein the agent adheres to the toilet bowl or urinal and can be flushed away only after a relatively large number of flushing operations, wherein the agent comprises fillers from the group of surfactants and also an adhesion promoter, wherein the adhesion promoter is selected from the group of polyalkylene derivatives which comprise polyalkylene chains with randomly distributed functional groups, or from the group of copolymers from the group of monoalkylesters of poly/methyl vinylethers/carboxylic anhydrides, olefin homopolymers and copolymers of two or more olefins being partially oxidized or further functionalized via graft molecules, and from the group of polyalkyleneimines, alkoxylated polyalkyleneimines, polyether amines or alkoxylated amines and polyglycerol polyether alkylcarboxylic acids or polymers or derivatives containing these polymer groups, wherein the viscosity of the agent is at least 30 Pas, measured using a Haake viscometer, plate/plate system, plate diameter 10 mm, at a shear gradient of 2.62 s⁻¹ and 20° C. and the agent is so sticky that it can serve to attach bar-shaped agents to the toilet bowl or urinal, wherein the concentration of the surfactants is between 10 and 80% by weight.

3. The method as claimed in claim 2, wherein the agent has a mass, wherein the object has a mass, and wherein the mass of the agent applied to the object is 3 to 15% by weight of the mass of the object.

4. The method as claimed in claim 1 or 2, characterized in that the polyalkylene chains of the adhesion promoters from the group of polyalkylene derivatives are selected from the group consisting of polybutadiene, polyisopropylene and polypropylene chains.

5. The method as claimed in claim 4, characterized in that the functional groups are selected from the group consisting of anhydrides, thiols, epoxides and primary amines.

6. The method as claimed in claim 4, characterized in that the polyalkylene derivatives are polymers with maleic anhydride groups bonded randomly to the polybutadiene chain and preferably the maleic anhydride adduct onto 1,4-cis-polybutadiene.

7. The method as claimed in claim 1 or 2, characterized in that the adhesion promoter from the group of olefin homopolymers and the copolymers from two or more olefins which are partly oxidized or further functionalized are selected from the group of polybutadiene rubbers, styrene-butadiene block polymers and copolymers, polyisoprenes, random block polymers which are prepared by 1,3-addition of butadiene or isoprene onto styrene or alpha-methylstyrene, homopolymers or copolymers of ethylene and propylene, such as ethylene-propylenediene terpolymers, ethylene-ethylene oxide copolymers, natural rubber and norbornene polymers such as polydicyclopentadiene.

8. The method as claimed in claim 1 or 2, characterized in that the adhesion promoters from the group of polyalkyleneimines are homopolymeric polyalkyleneimines, in particular of the general formula —(R—NH)$_n$ where R=alkyl or alkyl derivative, n=10-10⁵ with a two- or three-dimensional crosslinking on the nitrogen function.

9. The method as claimed in claim 8, characterized in that the polyalkyleneimines contain, as alkylene group, an ethylene, methylene, propylene, butylene or higher alkylene group.

10. The method as claimed in claim 1 or 2, characterized in that the polyether amines are alkoxylated primary and/or secondary and/or tertiary alkyl- or arylamines.

11. The method as claimed in claim 1 or 2, characterized in that the polyether amines contain tri-, bi- and/or monofunctional primary amines and, as polyether groups, polyethylene oxide, mixed poly(ethylene oxide/propylene oxide) or polypropylene oxide groups.

12. The method as claimed in claim 1 or 2, characterized in that the polyglycerol polyether alkylcarboxylic acids are selected from the group of polyethylene glycol-150 polyglyceryl-2 tristearate or PEG-150 diglyceryl tristearate or PEG-150 tetraglyceryl distearate.

13. The method as claimed in claim 1 or 2, characterized in that the concentration of the adhesion promoter in the agent is between 2% by weight and 60% by weight, preferably between 7 and 50% by weight and particularly preferably between 8% by weight and 40% by weight.

14. The method as claimed in claim 1 or 2, characterized in that the concentration of the adhesion promoter in the agent is between 15% by weight and 80% by weight, preferably between 20 and 70% by weight and particularly preferably between 30% by weight and 50% by weight.

15. The method as claimed in claim 1 or 2, characterized in that the fillers further comprise thickeners, fragrances, dyes, salts, foam stabilizers, foam boosters, or foam generators.

16. The method as claimed in claim 1 or 2, characterized in that the surfactant fraction in the agent is between 10 to 60% by weight and preferably 25 to 45% by weight.

17. The method as claimed in claim 1 or 2, characterized in that the surfactants are pulverulent or highly pasty.

18. The method as claimed in claim 1 or 2, characterized in that the surfactants are anionic surfactants and are selected from the group of salts of carboxylic acids, sulfuric acid half-esters, and sulfonic acids.

19. The method as claimed in claim 1 or 2, characterized in that the surfactants are nonionic surfactants and are selected from the group of alcohol ethoxylates, alkyl glycosides, alkoxylated fatty acid alkyl esters, amine oxides and alkanolamides.

20. The method as claimed in claim 15, characterized in that the agent comprises fragrances or perfume oils in a concentration between 0.25% by weight and 20% by weight, preferably between 3% by weight and 15% by weight and particularly preferably between 5% by weight and 10% by weight.

21. The method as claimed in claim 15, characterized in that the agent comprises up to 90% by weight of salts, in particular up to 10% by weight, preferably up to 5% by weight, of salts, preferably from the group of alkali metal and alkaline earth metal salts of strong acids or of mono-, di- and polycarboxylic acids.

22. The method as claimed in claim 15, characterized in that the agent comprises thickeners from the group of bentonites, powder surfactants, xanthans, polybutadiene rubbers, polyisopropenes, block copolymers, aryl ethoxylates or alkyl-aryl ethoxylates.

23. The method as claimed in claim 1 or 2, characterized in that the agent is a water-soluble and/or water-dispersible temporarily adhering adhesive.

24. The method as claimed in claim 1 or 2, characterized in that the agent comprises cleaning and/or deodorization and/or bleaching and/or coloring additives.

25. The method as claimed in claim 1 or 2, characterized in that the agent is ointment-like, pasty and/or cream-like and dimensionally stable.

26. The method as claimed in claim 1 or 2, characterized in that the surface tension of the agent is between 50 and 65 mN/m, in particular below 60 mN/m.

* * * * *